(12) United States Patent
Koeth

(10) Patent No.: US 8,879,599 B2
(45) Date of Patent: Nov. 4, 2014

(54) SEMICONDUCTOR LASER WITH ABSORBER APPLIED TO A LASER MIRROR

(75) Inventor: Johannes Bernhard Koeth, Gerbrunn (DE)

(73) Assignee: nanoplus GmbH Nanosystems and Technologies, Gerbrunn (DE)

(*) Notice: Subject to any disclaimer, the term of this patent is extended or adjusted under 35 U.S.C. 154(b) by 0 days.

(21) Appl. No.: 13/391,449

(22) PCT Filed: Aug. 11, 2010

(86) PCT No.: PCT/EP2010/061687
§ 371 (c)(1),
(2), (4) Date: Mar. 27, 2012

(87) PCT Pub. No.: WO2011/023551
PCT Pub. Date: Mar. 3, 2011

(65) Prior Publication Data
US 2012/0177075 A1    Jul. 12, 2012

(30) Foreign Application Priority Data
Aug. 26, 2009 (DE) .......... 10 2009 028 909

(51) Int. Cl.
  *H01S 5/00* (2006.01)
  *H01S 5/028* (2006.01)
  *G01N 21/39* (2006.01)
  *H01S 5/20* (2006.01)
  *H01S 5/026* (2006.01)

(52) U.S. Cl.
  CPC ............... *H01S 5/028* (2013.01); *H01S 5/005* (2013.01); *H01S 5/0014* (2013.01); *H01S 5/0287* (2013.01); *G01N 21/39* (2013.01); *H01S 5/2022* (2013.01); *H01S 5/026* (2013.01)

USPC ...................................... 372/49.01; 372/50.1

(58) Field of Classification Search
CPC ...... H01S 5/005; H01S 5/0281; H01S 5/0287
USPC ............................................ 372/49.01, 50.1
See application file for complete search history.

(56) References Cited

U.S. PATENT DOCUMENTS

| 4,503,541 | A | 3/1985 | Weller et al. |
| 7,573,928 | B1 * | 8/2009 | Pezeshki ............ 372/50.11 |

(Continued)

FOREIGN PATENT DOCUMENTS

| DE | 19908426 | 9/2000 |
| FR | 2753794 | 3/1998 |

(Continued)

OTHER PUBLICATIONS

International Search Report in Application No. PCT/EP2010/061687 dated Sep. 29, 2010, 3 pages.

*Primary Examiner* — Tod T Van Roy
(74) *Attorney, Agent, or Firm* — Meyertons Hood Kivlin Kowert & Goetzel, P.C.; Jeffrey C. Hood

(57) ABSTRACT

The invention relates to a semiconductor laser having at least one semiconductor substrate (10), at least one active layer (20) arranged on the semiconductor substrate (10) which generates radiation in a wavelength region, at least one laser mirror (40) which is applied at one end of the active layer (20) perpendicular thereto, through which a part of the radiation generated in the active layer (20) emerges, and which is provided with a layer of absorbing material (50, 60) said layer being suitable for reducing a gradient of the luminous-power/current characteristic for radiation emerging through the laser mirror (40).

36 Claims, 5 Drawing Sheets

(56) References Cited

U.S. PATENT DOCUMENTS

2001/0022796 A1* 9/2001 Okada et al. .................. 372/49
2008/0309218 A1 12/2008 Kamikawa et al.

FOREIGN PATENT DOCUMENTS

| | | |
|---|---|---|
| JP | 55-043822 | 3/1980 |
| JP | 01-254841 | 10/1989 |
| JP | 02-214182 | 8/1990 |
| JP | 04-207091 | 7/1992 |
| JP | 05-037072 | 2/1993 |
| JP | 05-075214 | 3/1993 |
| JP | 07-045910 | 2/1995 |
| JP | 2001-133403 | 5/2001 |
| JP | 2001-257413 | 9/2001 |
| JP | 2003-133648 | 5/2003 |
| JP | 2009-021548 | 1/2009 |
| WO | 2009/080012 | 7/2009 |

* cited by examiner

SEMICONDUCTOR LASER WITH ABSORBER APPLIED TO A LASER MIRROR

1. TECHNICAL SUBJECT AREA

The present invention relates to a semiconductor laser having an absorber applied to a laser mirror for suppressing the radiation emitted through the laser mirror.

2. PRIOR ART

Semiconductor lasers are already playing an important role in many areas of the economy as coherent light sources with high efficiency. They are used in applications in, for example, the telecommunications field and in the area of sensor technology.

Normally, due to their structure semiconductor lasers emit light via two cleavage surfaces of the semiconductor crystal, which act as laser mirrors. In general however, only the radiation coupled out via one laser mirror is collected for further use by means of optical elements. This useful light is normally emitted by the frontal mirror. The radiation emitted by the rear laser mirror represents a source of loss, which restricts the efficiency of the radiation source. In order to minimise this loss, the rear laser mirror is frequently also mirrored. However, even a laser diode mirrored on its rear side still only emits at least a few percent of the useful luminous power through the rear laser mirror.

Semiconductor lasers are normally mounted in a housing such that the frontal laser mirror is facing towards the optical element used to image the optical beam. The rear laser mirror on the other hand very often points in the direction of one or more parts of the housing. The photons exiting the laser diode through the rear laser mirror are at least partially reflected by the housing parts. Via multiple reflections, a part of the light emitted by the rear laser mirror can reach the imaging optical element, which collects the light emitted from the front face. The coupling of this scattered light into the useful optical radiation degrades its coherence characteristics and in the case of laser diodes driven in a modulated manner, leads to an uncontrollable temporal fluctuation in the light intensity and with laser diodes operated with constant injection current to a drift in the optical output luminous power.

In the sensor technology field, in particular in gas sensors, extremely small concentrations or traces of a molecule in the ppm-range (parts per million) must be able to be reliably detected in the atmosphere. The technique of tunable diode laser spectroscopy (TDLS) can be successfully applied here. An essential prerequisite for the use of TDLS is that laser diodes can be produced which essentially emit light of a single natural frequency of the laser resonator. The detection of the different molecules in TDLS occurs by excitation of rotational vibration transitions characteristic of each molecule by means of laser diodes. The excitation of the rotational vibration transitions extracts from the light beam individual photons at the characteristic frequency of the molecular transition. This results in two additional important prerequisites for the use of laser diodes in the field of gas sensor technology: the line width of the exciting semiconductor laser must be very narrow, i.e. comparable with the line width of the rotational vibration transitions of the molecules to be detected. In addition, the emission wavelength must be able to be tuned exactly to the transition or transitions and able to be tuned in a defined manner over a range covering the transition or transitions. As disclosed in patent document EP 0 985 535 B1, DFB (distributed feedback) laser diodes with lateral coupling satisfy all the above cited prerequisites.

The uncontrolled coupling of scattered light into the light beam of the frontal laser mirror, however, can degrade the quality of the useful signal for detecting extremely small concentrations of a molecule, and can thereby noticeably degrade the detection sensitivity of a sensor device having a DFB laser diode as the light source.

The problem addressed by the invention therefore is to specify measures which prevent radiation emitted as scattered light by the rear laser mirror from being coupled into the useful light beam.

3. SUMMARY OF THE INVENTION

According to one exemplary embodiment of the present invention this problem is solved by a device according to claim 1. In one embodiment the device comprises a semiconductor laser having at least one semiconductor substrate, at least one active layer arranged on the semiconductor substrate and at least one laser mirror, which is arranged at one end of the active layer and through which a part of the radiation generated in the active layer emerges, wherein the laser mirror is provided with a layer of absorbing material which is suitable for reducing a gradient of the luminous power/current characteristic for radiation which emerges through the laser mirror.

According to a further exemplary embodiment of the present invention this problem is solved by a device according to claim 2. In a further embodiment the device comprises a semiconductor laser having at least one semiconductor substrate, at least one active layer arranged on the semiconductor substrate and at least one laser mirror which is arranged at one end of the active layer and through which a part of the radiation generated in the active layer emerges, and an absorber module arranged on the semiconductor substrate which is arranged at a distance from the laser mirror in the direction of the generated radiation and which is suitable for reducing a gradient of the luminous power/current characteristic behind the absorber module for radiation which emerges through the laser mirror.

The layer of absorbing material on the rear laser mirror and/or the absorber module absorb radiation after it has passed through the rear laser mirror, and convert it into heat. Only a few photons can now exit this absorber layer and/or the absorber module and arrive at the rear parts of the housing. The number of photons which is actually coupled into the useful light beam as scattered light is negligible. Any deterioration in the coherence characteristics of the useful light beam due to scattered light originating from the rear laser mirror is eliminated. Applications in sensor technology are no longer adversely affected in terms of their detection sensitivity by a deterioration of the beam quality of the useful signal.

The application of the principles according to the invention is not limited to laser diodes. They can also be applied to LEDs (light emitting diodes).

In addition, the arrangement of the absorber module on the semiconductor substrate is not mandatory. It is also conceivable to mount the absorber module on one part or on different parts of the housing, for example on the mounting plate of the laser diode.

In a preferred embodiment the layer of absorbing material and/or the absorber module reduce the gradient of the luminous-power/current characteristic by a factor of 1,000, preferably by a factor of 10,000 and most preferably by a factor of 100,000.

In a further preferred embodiment the layer of absorbent material and/or the absorber module comprises one or more semiconductor materials and/or semiconductor compounds which absorb in the wavelength range of the generated radiation, carbon or carbon compounds and/or one or more paints or one or more lacquers.

In a particularly preferred embodiment, at least one electrical insulation layer is arranged between the laser mirror and the layer of absorbing material.

In a particularly highly preferred embodiment, the layer of absorbing material comprises one or more metals, in particular titanium. In a further particularly highly preferred embodiment, the absorber module comprises one or more metals, in particular titanium.

In a further particularly preferred embodiment, at least one reflection layer is arranged between the laser mirror and the layer of absorbing material or the absorber module.

In a preferred wavelength the reflection coefficient of the reflection layer in the emitted wavelength range is ≥90%.

In a further preferred embodiment the dielectric reflection layer comprises at least one metal oxide, such as aluminium oxide, magnesium oxide and/or titanium oxide. In addition, in a further preferred embodiment the reflection layer comprises at least one semiconductor material, for example silicon, a semiconductor compound, for example silicon dioxide, and/or a layer structure made of a semiconductor material and a semiconductor compound.

In a preferred embodiment, at least one electrical insulation layer is arranged between the laser mirror and the reflection layer. In a further preferred embodiment, a reflection layer is arranged between the laser mirror and the electrical insulation layer.

In a still further preferred embodiment, at least one electrical insulation layer is arrangedr between the reflection layer and the layer of absorbing material.

In a further preferred embodiment a reflection layer comprises at least one metal, in particular gold or silver.

In a further embodiment the absorber module, which is arranged at a distance behind the laser mirror, has a surface perpendicular to the light beam, onto which at least 99.9% of the light intensity emerging through the laser mirror is incident.

In one preferred embodiment the absorber module is provided on at least one side, which faces away from the laser mirror, with a layer of absorbing material. In a further preferred embodiment the entire surface of the absorber module is provided with a layer of absorbing material.

In addition, in one preferred embodiment the absorber module is produced on the semiconductor substrate by means of an epitaxial process. In a further preferred embodiment the absorber module is attached to the semiconductor substrate by adhesive bonding or soldering.

In addition, in a further preferred embodiment the semiconductor laser, which has at least one semiconductor substrate, at least one active layer arranged on the semiconductor substrate and at least one laser mirror arranged at one end of the active layer and through which a part of the radiation generated in the active layer emerges, wherein the laser mirror is provided with a layer of absorbing material which is suitable for reducing a gradient of the luminous-power/current characteristic for radiation which emerges through the laser mirror, comprises an absorber module arranged on the semiconductor substrate (10) arranged at a distance from the laser mirror in the direction of the generated radiation and which is suitable for reducing a gradient of the luminous-power/current characteristic behind the absorber module, for radiation which emerges through the laser mirror.

In a quite particularly preferred embodiment a sensor device for determining gas concentrations has a semiconductor laser according to one of the preceding embodiments.

4. DESCRIPTION OF THE DRAWINGS

In the following detailed description, currently preferred exemplary embodiments of the invention are described by reference to the drawings, in which FIG. 1 shows a schematic illustration of the components of a semiconductor laser most important to the invention, wherein the semiconductor laser has a layer of absorbing material on the rear laser mirror;

FIG. 2 shows a schematic illustration of the components of a semiconductor laser most important to the invention, wherein an absorber module is arranged on the semiconductor substrate at a distance from the rear laser mirror;

FIG. 3 reproduces FIG. 1 with an electrical insulation layer between the rear laser mirror and the layer of absorbing material;

5. DETAILED DESCRIPTION OF PREFERRED EXEMPLARY EMBODIMENTS

In the following, preferred embodiments of the devices according to the invention are explained in more detail.

Figure 1:
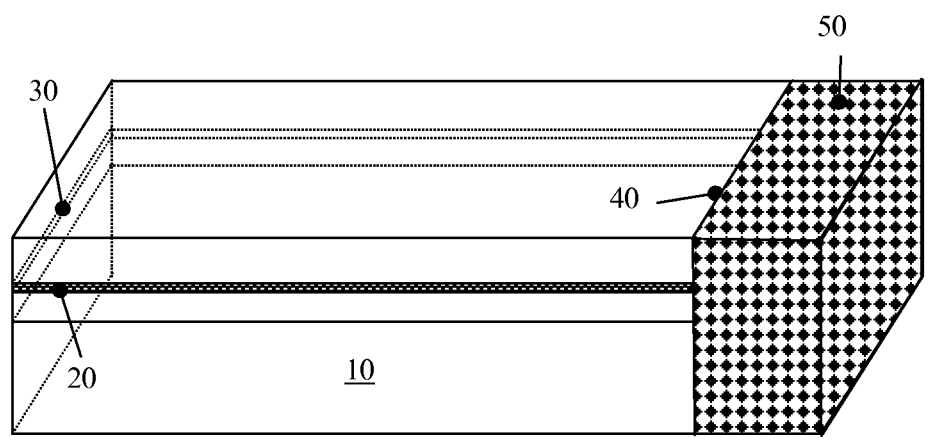

FIG. 1 shows a schematic view of the layers of a semiconductor laser which are important to the explanation of the principles according to the invention. On a semiconductor substrate 10, a waveguide structure (not shown in FIG. 1) is deposited by means of an epitaxial process, into which an active layer 20 is embedded. In the active layer 20 optical radiation is generated in a wavelength range within the amplification bandwidth of the material of the active layer 20. The active layer is terminated on the front face of the laser by a frontal mirror 30 and on the opposite side by the rear laser mirror 40. The active layer 20 does not, as shown in FIG. 1, have to extend as far as the laser mirrors 30, 40. In particular, the current which is injected into the active layer 20 does not need to be supplied over the entire length between the laser mirrors 30 and 40.

In addition to or instead of the laser mirrors 30 and 40, which form a Fabry-Perot resonator, the semiconductor laser can comprise additional wavelength-selecting elements, such as a DFB (distributed feedback) or a DBR (distributed Bragg reflection) structure. The layer of absorbing material according to the invention, like the absorber module according to the invention described in the following, can also be used for laser diodes which emit light in the direction of the layer sequence, i.e. for so-called VCSELs (vertical cavity surface emitting lasers). In addition, the use of the layer of absorbing material according to the invention, and of the absorber module described below as well, is not restricted to laser diodes; the principles according to the invention—as already mentioned—can also be applied to LEDs.

The material system of the semiconductor substrate 10 is determined by the wavelength of the laser diode to be realised. The principles according to the invention described in detail below can be applied to all known material systems, in order to produce laser diodes or all types of LEDs which emit light from the blue wavelength range (for example on gallium nitride substrates) to deep into the infrared range. As well as substrates based on III/V compound semiconductors the principles disclosed can also be applied to laser diodes or LEDs which are assembled on II/VI semiconductor substrates or other suitable substrates. It is furthermore possible to employ the principles according to the invention to light-emitting components which are formed from organic and semiconducting materials and which are known under the acronym OLED (organic light emitting diode).

A layer of absorbing material 50 is applied to the rear laser mirror 40 with the aim being that radiation which permeates through the laser mirror 40 into the absorbent layer 50 is absorbed by the material of this layer and converted into heat. In laser diodes with Fabry-Perot resonators, the refractive index of the absorbing layer 50 must not be identical to the refractive index of the active layer 20, otherwise the effect of the laser mirror 40 would be lost and the semiconductor radiation source would no longer function as a laser diode. If the numerical value of the absorption coefficient of the absorbent layer 50 is large, a small layer thickness 20 is sufficient to obtain a specified residual transmission. Conversely, a large absorption coefficient means that the whole of the radiation power is converted into heat in a small volume.

Figure 2:
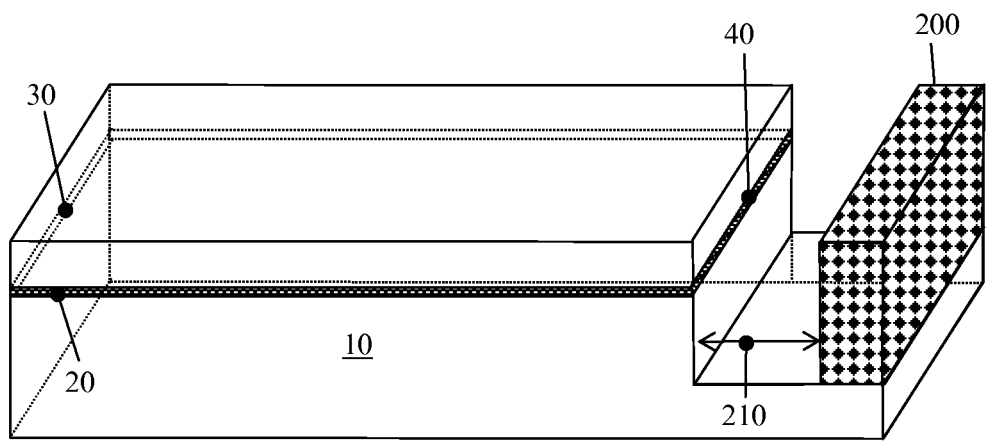

FIG. 2 shows the semiconductor laser illustrated in FIG. 1 in which the layer structure towards the rear part—including the active layer 20—has been removed to leave only parts of the semiconductor substrate 10. Behind the rear laser mirror 40, at a distance 210 from the laser mirror 40, an absorber module 200 is arranged on the semiconductor substrate 10. The distance 210 and the surface of the absorber module 200 perpendicular to the direction of the light beam are chosen such that at least 99.9% of the photons which exit the laser resonator through the laser mirror 40 are incident on the absorber module 200. If the distance 210 is small, this requirement is fulfilled by a small area of the absorber module 200 facing the laser mirror 40. With increasing distance 210, the surface area of the absorber module 200 facing the laser mirror 40 must increase correspondingly.

The absorber module 200 can be produced on the semiconductor substrate 10 by means of an epitaxial process. It is also possible, however, to attach a pre-fabricated absorber module 200 on the semiconductor substrate 10 or on a sub-mount which is spatially separated from the semiconductor material, for example by adhesive bonding or soldering. The absorber module 200 does not need to have—as shown in FIG. 2—a parallelipipedal shape. Any desired shapes of the absorber module can be used. By arranging the absorber module 200 at a distance 210 from the rear laser mirror 40, a thermal loading of the laser mirror 40 due to a possible heating of the absorbent material, in particular at high optical power levels and with a large absorption coefficient, can be prevented.

As absorber materials for both the layer of absorbing material of FIG. 1 and the absorber module 200 of FIG. 2, a semiconductor material 20 or a combination of a plurality of semiconductor materials which absorb in the wavelength range of the generated laser radiation can be used. For wavelengths of the optical radiation less than 1 µm, silicon can be used, for example. Semiconductor compounds, which due to their small band gap can absorb light of longer wavelengths, are, for example, indium arsenide and indium antimonide.

In addition, absorbing materials can be produced that are based on carbon, in particular amorphous carbon, for example in the form of carbon black. Also, carbon compounds can be used as starting materials for absorber materials. In addition, paints or lacquers can be applied for generating absorbent layers for the wavelength range discussed, from approximately 0.5 µm to approximately 10 µm.

Figure 4:
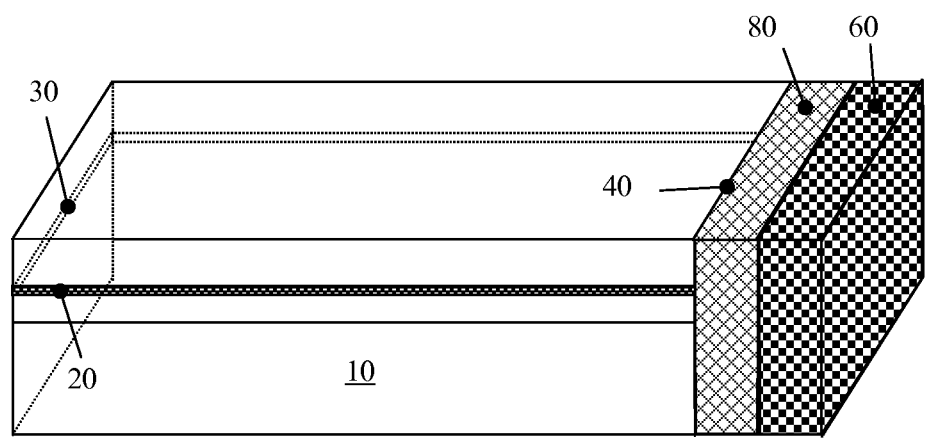
FIG. 4 illustrates FIG. 1 with a reflection layer between the rear laser mirror and the layer of absorbing material.

In FIG. 4 an electrical insulation layer 70 has been incorporated between the laser mirror 40 and the layer of absorbing material 60 of FIG. 1. This additional layer performs two functions: firstly, the absorbent layer 60 is electrically decoupled from the laser mirror 40. This makes it possible to use conductive materials such as metals as the absorber material, for example titanium or a combination of more than one metal. Due to the high absorption coefficients of most metals in the wavelength range of approximately 0.5 µm to approximately 10 µm, even thin layers in the region of a few 100 nm are sufficient to absorb almost all the photons. Secondly, the choice of the material of the electrical insulation layer 70 allows the difference in the refractive index between the semiconductor material of the laser mirror 40 and the insulation layer 70, and thereby the reflection factor of the laser mirror 40, to be adjusted in a defined manner.

For the absorber module 200 of FIG. 2, one or more metals can also be used.

The exemplary embodiments discussed so far effectively suppress the radiation of the rear laser mirror and thus prevent the problems due to scattered light described in the second section. A problem can arise, however, if the refractive index of the absorbing layer 50 or of the electrical insulation layer 70 is markedly greater than 1. This can lead to the reflection factor of the rear laser mirror 40 being reduced relative to its starting value. The quality of the laser resonator is thereby degraded and the component of the luminous power coupled out via the rear laser mirror increases. A particularly advantageous embodiment of the principles according to the invention therefore combines a reflection coating applied to the rear laser mirror 40 with a layer of absorbing material 50, 60 behind the reflection coating.

Figure 3:
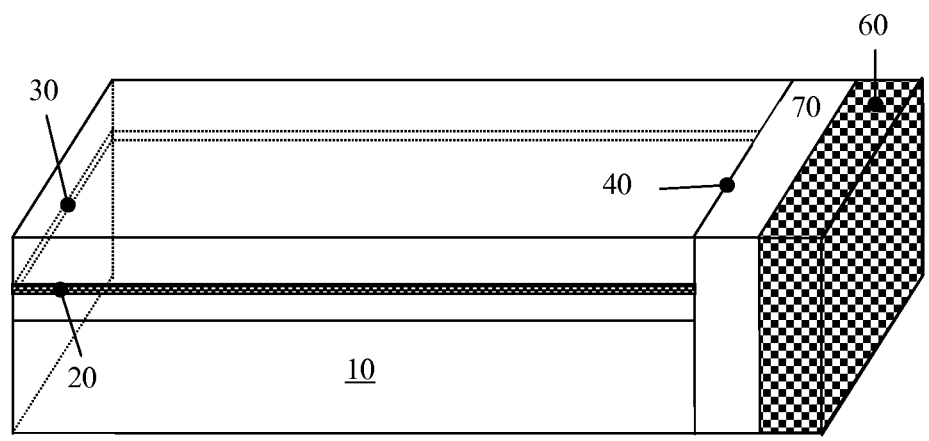

FIG. 3 shows a schematic view of this embodiment. With the reflection layer 80, which can comprise one or more dielectric layers, the reflection factor of the rear laser mirror 40 can be adjusted. In particular, by enhancing the rear laser mirror 40 by means of the reflection layer 80, the reflection factor of the rear laser mirror 40 can be increased beyond its original value. Reflection factors in the region of 90% to 95% are achievable by the application of one or more dielectric layers. A large reflection factor of the reflection layer 80 has two advantages: firstly, the source of loss represented by the rear laser mirror 40, is reduced in size. This results in an increase in the efficiency of the semiconductor laser. Secondly, less luminous power needs to be transformed into heat in the layer of absorbing material 50, 60 following the reflection layer 80. Thus, for a specified permitted residual transmission the absorbent layer 50, 60 can be made thinner, or for a constant thickness of the layer of absorbing material 50, 60, the number of photons which manage to penetrate a layer 50, 60 decreases.

The advantages of a reflection layer 80 described in the previous section but one are produced in the same manner for the combination of a laser mirror 40, which is provided with a reflection layer 80 and with the absorber module 200 shown in FIG. 2. The photons which exit the reflection layer 80, after they are incident on the absorber module 200, are converted into heat by the absorbent material of the absorber module 200.

Figure 5:
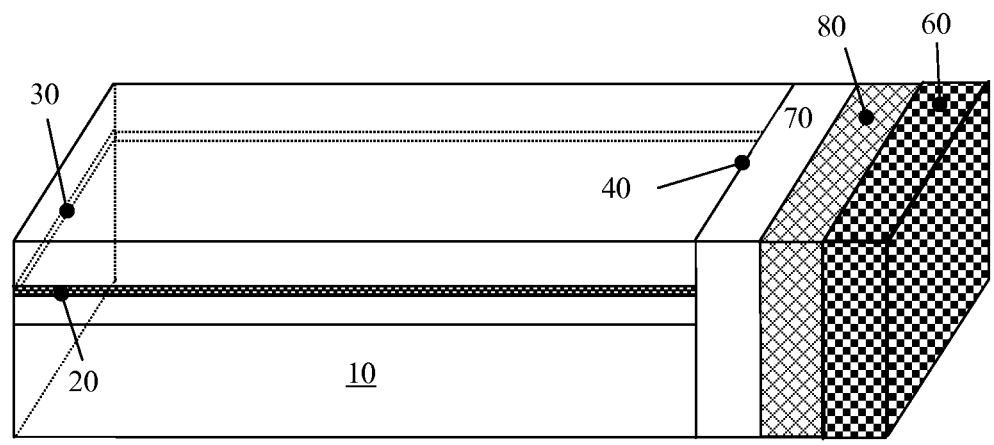
FIG. 5 shows FIG. 4 with an electrical insulation layer between the rear laser mirror and the reflection layer.

In FIG. 5, in addition to the reflection layer 80 and the layer of absorbing material 50, 60, the electrical insulation layer 70 of FIG. 3 has been inserted between the laser mirror 40 and the reflection layer 80. This means that the step change in refractive index at the laser mirror 40 and at the reflection layer 80 can be adjusted. In addition, the electrical insulation layer 70 enables the maximum of the intensity distribution to be shifted from the laser mirror 40 into the insulation layer 70. This protects the rear laser mirror 40 against damage, in particular when high luminous power levels are coupled out through the frontal laser mirror 30.

Figure 6:
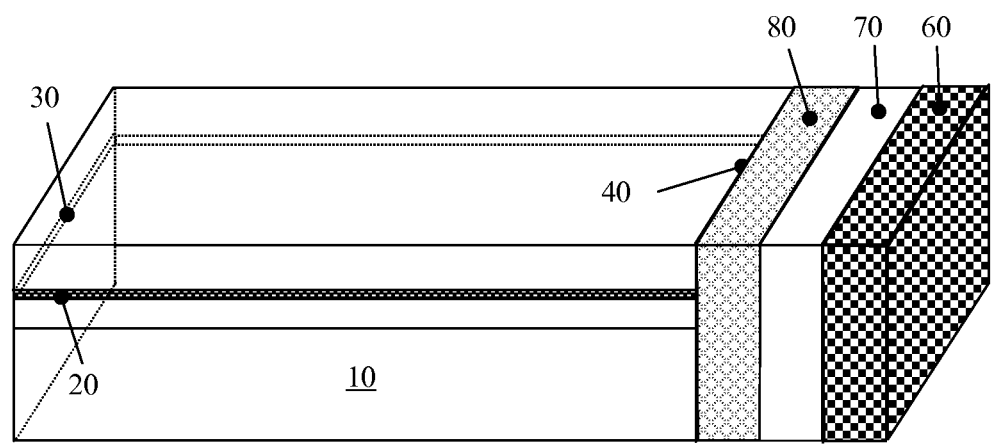
FIG. 6 illustrates FIG. 5, wherein the order of the electrical insulation layer and reflection layer have been reversed.

In FIG. 6 the sequence of the two layers, the electrical insulation layer 70 and reflection layer 80, has been reversed compared to that of FIG. 5. This opens up greater freedom in the choice of the materials for the layer of absorbing material 50, 60. In particular, the layer of absorbing material 50, 60 can comprise one or more metals.

Figure 7:
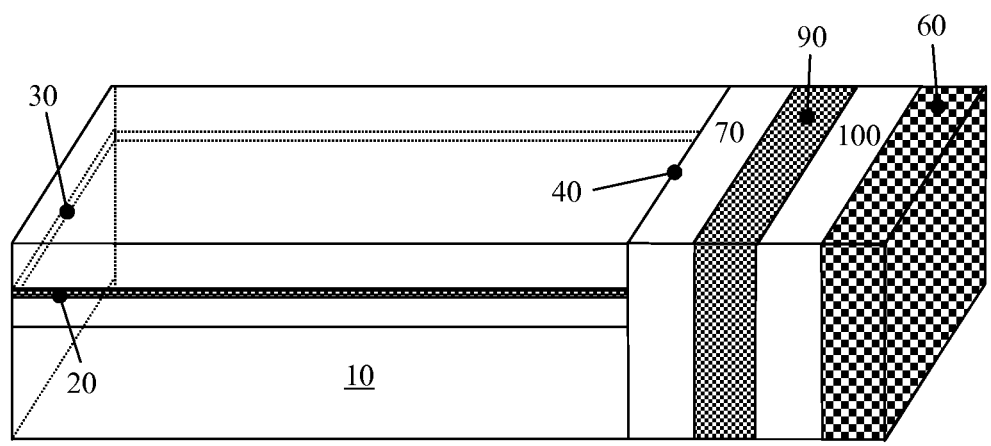
FIG. 7 represents FIG. 5 with an electrical insulation layer between the reflection layer and the layer of absorbing material.

FIG. 7 shows a schematic view of FIG. 5 with an additional electrical insulation layer 100 between the reflection layer 80 and the layer of absorbing material 50, 60. This additional insulation layer 100 decouples the reflection layer 80 from the layer of absorbing material 50, 60. With the layer arrangement shown in FIG. 7 it becomes possible to use a wide range of materials both for the reflection layer 90 and the layer of absorbing material 50, 60, in particular one or more metals or metal compounds. This applies equally to the reflection layer 90 and to the layer of absorbing material 60.

In addition, it is possible to use a combination of a layer of absorbing material 50, 60 and an absorber module 200. By only a part of the luminous power in the immediate vicinity of the laser mirror 40 being converted into heat, the thermal loading of the laser mirror 40 at very large optical power levels is limited. It is further conceivable to combine all of the layer sequences discussed above—electrical insulation layers 70, 100, reflection layer 80 and layers of absorbing material 50, 60—with an absorber module 200.

Due to the reflective coating of the rear laser mirror 40, the luminous power that emerges through the rear laser mirror 40 falls in comparison to the optical power that exits the laser resonator through the frontal laser mirror 30. Due to the anti-reflection coating of the frontal laser mirror 30 being used simultaneously with a reflective coating of the rear laser mirror 40, the luminous power that can be coupled out from the front face of the laser resonator is further increased.

Figure 8:
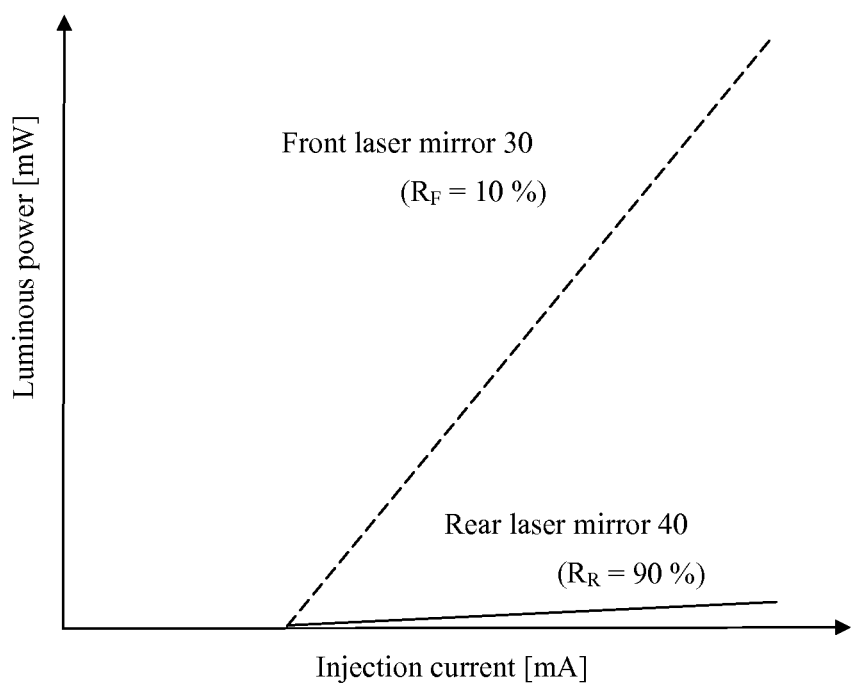
FIG. 8 shows luminous-power/current characteristics of a semiconductor laser with a laser mirror that is anti-reflection coated on its front face ($R_F$=10%) and a laser mirror mirrored on its rear face ($R_R$=90%)

FIG. 8 reproduces the calculated values for the luminous-power/current characteristic of a semiconductor laser for which the frontal laser mirror 30 has a reflection coefficient of 10% and the rear laser mirror 40 a reflection coefficient of 90%. The asymmetry of the luminous powers coupled out from the front and the rear faces is in the region of approximately 30. This means that, in spite of the anti-reflection coating of the frontal laser mirror 30 and a highly reflective coating of the rear laser mirror 40, between 3% and 4% of the luminous power still leaves the laser resonator through the rear laser mirror 40.

Figure 9:
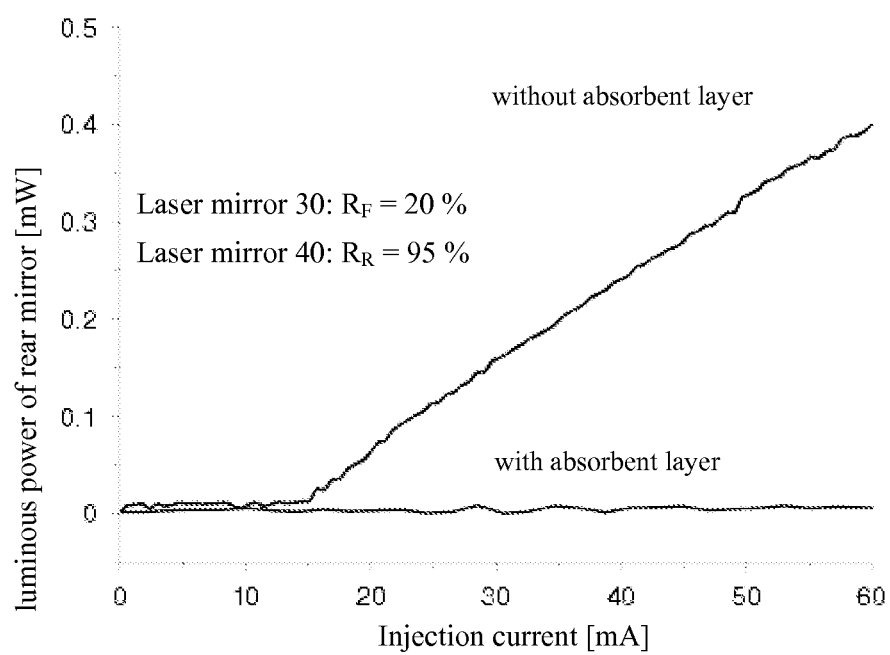
FIG. 9 shows luminous-power/current characteristics measured at a rear laser mirror with $R_R$=95% before and after coating with a layer of absorbing material, wherein the frontal laser mirror has a reflection coefficient of 20%.

FIG. 9 shows luminous-power/current characteristics of a GaSAs/$Al_xGa_{(1-x)}$As (gallium arsenide/aluminium-gallium arsenide) DFB laser diode with lateral coupling, measured at the rear laser mirror 40 before and after the application of a layer of absorbing material 60. In addition, the laser diode is anti-reflection coated on the frontal laser mirror 30 ($R_F$=20%) and mirrored on the rear laser mirror 40 ($R_R$=95%). This corresponds to the arrangement shown in FIG. 4 with an additional partial anti-reflective coating of the frontal laser mirror 30. In this example the absorbent layer 60 substantially consists of titanium and the reflection layer 80 comprises four sub-layers in the sequence $SiO_2$/Si/$SiO_2$/Si beginning at the laser mirror 40.

As can be seen from FIG. 9, after the application of the absorbent layer 60, luminous power can no longer be detected behind the rear laser mirror 40. The absorbent layer 60 of the rear laser mirror 40 reduces the gradient of the luminous-power//current characteristic measured after the laser mirror 40 in this example by at least a factor of 10,000. This figure only represents an estimate however, since by the combination of a highly mirrored rear laser mirror 40 ($R_R$=95%) with a layer of absorbing material 60, the gradient of the luminous-power//current characteristic behind the laser mirror 40 is reduced so much that an experimental determination of its gradient is no longer possible.

The electrical insulation layers 70, 100 and the reflection layer 80 can be applied to the rear laser mirror 40 by means of thermal vapour deposition, electron-beam vapour deposition or by means of a sputtering process. The layer of absorbing material 60 and the reflection layer 90 can be applied to the rear laser mirror 40 by means of thermal vapour deposition, electrical vapour deposition of the material or by means of a sputtering process.

The absorber module 200 can be assembled from the above described materials. It is also possible however to use a base structure made of any desired material for the absorber module, for example a glass or plastic body, and to provide at least the side facing the laser mirror 40 with a layer of absorbing material 50, 60 by means of a method described in the preceding section. The entire surface of the base structure can also be covered with a layer of absorbing material. Finally, further processes can be used to apply a layer of absorbing material to the base structure, thus for example the surface of the base structure can be sprayed with an absorbent material or the base structure is placed into an immersion bath which contains the absorbent material.

The following table contains examples of the coating data of the rear laser mirror 40 of the semiconductor laser used in FIG. 9.

TABLE 1

Data for the reflection layer 80 and the layer of absorbing material 60

| Function | Thickness [nm] | Material |
|---|---|---|
| Reflection layer 80 | 270 | SiO2 |
| | 110 | Si |
| | 270 | SiO2 |
| | 110 | Si |
| Layer of absorbing material 60 | 500 | Titanium |

The invention claimed is:

1. A semiconductor laser, comprising:
   a. at least one semiconductor substrate;
   b. at least one active layer arranged on the semiconductor substrate;
   c. at least one frontal laser mirror which is arranged at a first end of the active layer and through which a first part of the radiation generated in the active layer emerges; and
   d. at least one rear laser mirror which is arranged at a second end of the active layer and lying opposite the first end and through which a second part of the radiation generated in the active layer emerges, wherein the at least one rear laser mirror is provided with a layer of absorbing material, and wherein the layer of absorbing material is configured to reduce a gradient of the luminous-power/current characteristic for radiation emerging through the at least one rear laser mirror, relative to a rear laser mirror without a layer of absorbing material;

wherein a layer thickness of the layer of absorbing material is configured to reduce the gradient of the luminous-power/current characteristic by at least a factor of 1000;

wherein at least one reflection layer is arranged between the at least one rear laser mirror and the layer of absorbing material having a reflection coefficient in the emitted wavelength range ≥90%;

wherein at least one electrical insulation layer is arranged between the at least one rear laser mirror and the at least one reflection layer; and wherein the layer thickness of the layer of absorbing material and the reflection coefficient of the at least one reflection layer combine to reduce the second part of the radiation generated in the active layer emitted behind the layer of absorbing material to an undetectable level, thereby preventing the second part of the radiation from contaminating the first part of radiation.

2. The semiconductor laser according to claim 1, wherein the layer thickness of the layer of absorbing material is configured to reduce the gradient of the luminous-power/current characteristic by at least a factor of 10,000.

3. The semiconductor laser according to claim 1, wherein the layer of absorbing material comprises one or more of:
one or more semiconductor materials, configured to absorb radiation in the wavelength range of the first part of the radiation;
one or more semiconductor compounds, configured to absorb radiation in the wavelength range of the first part of the radiation;
carbon;
one or more carbon compounds; or
one or more absorbent lacquers.

4. The semiconductor laser according to claim 1,
wherein at least one electrical insulation layer is arranged between the at least one rear laser mirror and the layer of absorbing material.

5. The semiconductor laser according to claim 4, wherein the layer of absorbing material comprises one or more metals, wherein the one or more metals comprise titanium.

6. The semiconductor laser according to claim 1, wherein the at least one reflection layer comprises at least one metal oxide, wherein the at least one metal oxide comprises one or more of:
aluminum oxide;
titanium oxide;
magnesium oxide.

7. The semiconductor laser according to claim 1, wherein the at least one reflection layer comprises at least one of:
a semiconductor material;
a semiconductor compound; or
a layer structure comprising the semiconductor material and the semiconductor compound.

8. The semiconductor laser according to claim 7, wherein the at least one semiconductor material comprises silicon, and wherein the at least one semiconductor compound comprises silicon dioxide.

9. The semiconductor laser according to claim 1, wherein the at least one reflection layer is arranged between the at least one rear laser mirror and at least one electrical insulation layer.

10. The semiconductor laser according to claim 1, wherein at least one electrical insulation layer is arranged between the at least one reflection layer and the layer of absorbing material.

11. The semiconductor laser according to claim 10, wherein the at least one reflection layer comprises at least one metal, comprising one or more of:
gold; or
silver.

12. The semiconductor laser according to claim 1, further comprising:
an absorber module arranged on the semiconductor substrate, wherein the absorber module is arranged at a distance from the at least one rear laser mirror in the direction of the second part of the radiation, and wherein the absorber module is configured to reduce a gradient of the luminous power/current characteristic behind the absorber module for radiation which emerges through the at least one rear laser mirror.

13. The semiconductor laser according to claim 1, wherein the semiconductor laser is useable as a sensor device for determining gas concentrations.

14. A semiconductor laser, comprising:
a. at least one semiconductor substrate;
b. at least one active layer arranged on the semiconductor substrate;
c. at least one frontal laser mirror which is arranged at a first end of the active layer and through which a first part of the radiation generated in the active layer emerges; and
d. at least one rear laser mirror which is arranged at a second end of the active layer and lying opposite the first end and, through which a second part of the radiation generated in the active layer emerges; and
e. an absorber module arranged on the semiconductor substrate, wherein the absorber module is arranged at a distance from the at least one rear laser mirror in the direction of the second part of the radiation, wherein the absorber module is configured to reduce a gradient of the luminous power/current characteristic behind the absorber module for radiation emerging through the at least one rear laser mirror, relative to the gradient of the luminous-power/current characteristic behind the at least one rear laser mirror,
wherein a thickness of the absorber module is configured to reduce the gradient of the luminous-power/current characteristic by at least a factor of 1000;
wherein at least one reflection layer is arranged between the at least one rear laser mirror and the absorber module having a reflection coefficient in the emitted wavelength range ≥90%;
wherein at least one electrical insulation layer is arranged between the at least one rear laser mirror and the at least one reflection layer; and
wherein the thickness of the absorber module and the reflection coefficient of the at least one reflection layer combine to reduce the second part of the radiation generated in the active layer emitted behind the absorber module to an undetectable level, thereby preventing the second part of the radiation from contaminating the first part of radiation.

15. The semiconductor laser according to claim 14, wherein the thickness of the absorber module is configured to reduce the gradient of the luminous-power/current characteristic by a factor of 10,000.

16. The semiconductor laser according to claim 14, wherein the absorber module comprises one or more of:

one or more semiconductor materials, configured to absorb radiation in the wavelength range of the first part of the radiation;
one or more semiconductor compounds, configured to absorb radiation in the wavelength range of the first part of the radiation;
carbon;
one or more carbon compounds; or
one or more absorbent lacquers.

17. The semiconductor laser according to claim 14,
wherein at least one electrical insulation layer is arranged between the at least one rear laser mirror and the absorber module.

18. The semiconductor laser according to claim 14, wherein the absorber module comprises one or more metals, wherein the one or more metals comprise titanium.

19. The semiconductor laser according to claim 14, wherein the reflection layer comprises at least one metal oxide, and wherein the at least one metal oxide comprises one or more of:
aluminum oxide;
titanium oxide; or
magnesium oxide.

20. The semiconductor laser according to claim 14, wherein the at least one reflection layer comprises at least one of:
a semiconductor material;
a semiconductor compound: or
a layer structure comprising the semiconductor material and the semiconductor compound.

21. The semiconductor laser according to claim 20, wherein the at least one semiconductor material comprises silicon, and wherein the at least one semiconductor compound comprises silicon dioxide.

22. The semiconductor laser according to claim 14, wherein the at least one reflection layer is arranged between the at least one rear laser mirror and at least one electrical insulation layer.

23. The semiconductor laser according to claim 14, wherein at least one electrical insulation layer is arranged between the at least one reflection layer and the absorber module.

24. The semiconductor laser according to claim 23, wherein the at least one reflection layer comprises at least one metal, comprising one or more of:
gold; or
silver.

25. The semiconductor laser according to claim 14, wherein the absorber module is configured such that at least 99.9% of light intensity emerging through the rear laser mirror is incident on the absorber module.

26. The semiconductor laser according to claim 14, wherein the absorber module comprises at least one side facing towards the at least one frontal laser mirror, wherein the at least one side comprises a layer of absorbing material.

27. The semiconductor laser according to claim 14, wherein an entire surface of the absorber module comprises a layer of absorbing material.

28. The semiconductor laser according to claim 14, wherein the absorber module is produced on the semiconductor substrate by means of an epitaxial process.

29. The semiconductor laser according to claim 14, wherein the absorber module is attached to the semiconductor substrate by adhesive bonding or soldering.

30. The semiconductor laser according to claim 14, wherein the semiconductor laser is useable as a sensor device for determining gas concentrations.

31. A semiconductor laser, comprising:
a. at least one semiconductor substrate;
b. at least one active layer arranged on the semiconductor substrate;
c. at least one frontal laser mirror which is arranged at a first end of the active layer and through which a first part of the radiation generated in the active layer emerges; and
d. at least one rear laser mirror which is arranged at a second end of the active layer and lying opposite the first end and through which a second part of the radiation generated in the active layer emerges, wherein the at least one rear laser mirror is provided with a layer of absorbing material, and wherein the layer of absorbing material is configured to reduce a gradient of the luminous-power/current characteristic for radiation emerging through the at least one rear laser mirror, relative to a rear laser mirror without a layer of absorbing material;
wherein a layer thickness of the layer of absorbing material is configured to reduce the gradient of the luminous-power/current characteristic by at least a factor of 1000;
wherein at least one reflection layer is arranged between the at least one rear laser mirror and the layer of absorbing material having a reflection coefficient in the emitted wavelength range ≥90%;
wherein at least one electrical insulation layer is arranged between the at least one reflection layer and the layer of absorbing material; and
wherein the layer thickness of the layer of absorbing material and the reflection coefficient of the at least one reflection layer combine to reduce the second part of the radiation generated in the active layer emitted behind the layer of absorbing material to an undetectable level, thereby preventing the second part of the radiation from contaminating the first part of radiation.

32. The semiconductor laser according to claim 31, wherein the layer of absorbing material comprises one or more of:
one or more semiconductor materials, configured to absorb radiation in the wavelength range of the first part of the radiation;
one or more semiconductor compounds, configured to absorb radiation in the wavelength range of the first part of the radiation;
carbon;
one or more carbon compounds; or
one or more absorbent lacquers.

33. The semiconductor laser according to claim 31, wherein the layer of absorbing material comprises one or more metals, wherein the one or more metals comprise titanium.

34. A semiconductor laser, comprising:
a. at least one semiconductor substrate;
b. at least one active layer arranged on the semiconductor substrate;
c. at least one frontal laser mirror which is arranged at a first end of the active layer and through which a first part of the radiation generated in the active layer emerges; and
d. at least one rear laser mirror which is arranged at a second end of the active layer and lying opposite the first end and, through which a second part of the radiation generated in the active layer emerges; and
e. an absorber module arranged on the semiconductor substrate, wherein the absorber module is arranged at a distance from the at least one rear laser mirror in the direction of the second part of the radiation, wherein the absorber module is configured to reduce a gradient of the luminous power/current characteristic behind the absorber module for radiation emerging through the at least one rear laser mirror, relative to the gradient of the luminous-power/current characteristic behind the at least one rear laser mirror, wherein a thickness of the absorber module is configured to reduce the gradient of the luminous-power/current characteristic by at least a factor of 1000;

wherein at least one reflection layer is arranged between the at least one rear laser mirror and the absorber module having a reflection coefficient in the emitted wavelength range ≥90%;

wherein at least one electrical insulation layer is arranged between the at least one reflection layer and the absorber module; and wherein the thickness of the absorber module and the reflection coefficient of the at least one reflection layer combine to reduce the second part of the radiation generated in the active layer emitted behind the absorber module to an undetectable level, thereby preventing the second part of the radiation from contaminating the first part of radiation.

35. The semiconductor laser according to claim 34, wherein the layer of absorbing material comprises one or more of:
- one or more semiconductor materials, configured to absorb radiation in the wavelength range of the first part of the radiation;
- one or more semiconductor compounds, configured to absorb radiation in the wavelength range of the first part of the radiation;
- carbon;
- one or more carbon compounds; or
- one or more absorbent lacquers.

36. The semiconductor laser according to claim 34, wherein the absorber module comprises one or more metals, wherein the one or more metals comprise titanium.

* * * * *